(12) United States Patent  
Jiang (10) Patent No.: US 11,846,780 B2  
(45) Date of Patent: Dec. 19, 2023

(54) HEAD-MOUNTED ELECTRONIC VISION AID DEVICE AND AUTOMATIC IMAGE MAGNIFICATION METHOD THEREOF

(71) Applicant: Artheia Technologies (Suzhou) Co., Ltd., Suzhou (CN)

(72) Inventor: Haotian Jiang, Mill Neck, NY (US)

(73) Assignee: ARTHEIA TECHNOLOGIES (SUZHOU) CO., LTD., Suzhou (CN)

( * ) Notice: Subject to any disclaimer, the term of this patent is extended or adjusted under 35 U.S.C. 154(b) by 1 day.

(21) Appl. No.: 17/643,976

(22) Filed: Dec. 13, 2021

(65) Prior Publication Data  
US 2022/0390745 A1  Dec. 8, 2022

(30) Foreign Application Priority Data  
Jun. 3, 2021 (CN) .......................... 202110619230.6

(51) Int. Cl.  
G02B 27/01 (2006.01)  
A61F 9/08 (2006.01)  
H04N 13/344 (2018.01)

(52) U.S. Cl.  
CPC ............ *G02B 27/0172* (2013.01); *A61F 9/08* (2013.01); *G02B 27/0101* (2013.01); *H04N 13/344* (2018.05); *G02B 2027/0178* (2013.01)

(58) Field of Classification Search  
CPC ............ G02B 27/0172; G02B 27/0101; G02B 2027/0178; H04N 13/344; H04N 23/61;  
(Continued)

(56) References Cited

U.S. PATENT DOCUMENTS

2009/0136223 A1 * 5/2009 Motomura ............. H04N 23/67  
396/77  
2017/0246070 A1 8/2017 Osterhout et al.  
(Continued)

FOREIGN PATENT DOCUMENTS

CN 104717427 B * 6/2018  
CN 104717427 B   6/2018  
(Continued)

OTHER PUBLICATIONS

Extended European Search Report issued for European Patent Application No. 22158608.4, dated Jul. 28, 2022, 9 pages.

*Primary Examiner* — William C Vaughn, Jr.  
*Assistant Examiner* — Naod W Belai  
(74) *Attorney, Agent, or Firm* — Hamre, Schumann, Mueller & Larson, P.C.

(57) ABSTRACT

Disclosed in the present invention is a head-mounted electronic vision aid device and an image magnification method thereof. The head-mounted electronic vision aid device comprising a memory unit, a processing unit, an image zooming unit, and at least one ranging unit; the ranging unit being configured to obtain distance data between a target object of interest to a user and the device and/or three-dimensional profile data of the object and output the data to the processing unit; the memory unit stores a correspondence table between the distance data and the magnification of the image zooming unit; the processing unit confirms the target object of interest to the user, performs operations on the distance data and/or the three-dimensional profile data of the object, and outputs an magnification matching the distance data to the image zooming unit according to the correspondence table; and the image zooming unit can automatically adjust to the matching magnification. For visually impaired users, accurate, intuitive and rapid automatic magnification of the target objects of interest can be (Continued)

realized on demand. Compared with the prior art, the repeated and tedious manual adjustment is avoided, and the user experience is greatly improved.

19 Claims, 3 Drawing Sheets

(58) Field of Classification Search
CPC .. H04N 23/632; H04N 23/635; H04N 23/671; H04N 23/69; H04N 5/2226; A61F 9/08; G06F 3/011; G06V 20/647; G09B 21/008
See application file for complete search history.

(56) References Cited

U.S. PATENT DOCUMENTS

| | | |
|---|---|---|
| 2017/0318235 A1 | 11/2017 | Schneider et al. |
| 2018/0144554 A1 | 5/2018 | Watola et al. |
| 2019/0020823 A1* | 1/2019 | Jeon ................. G06V 40/20 |
| 2021/0240988 A1 | 8/2021 | Lim |

FOREIGN PATENT DOCUMENTS

| | | |
|---|---|---|
| CN | 109670445 | 4/2019 |
| WO | 2019231216 A1 | 12/2019 |
| WO | 2020068819 | 4/2020 |

\* cited by examiner

HEAD-MOUNTED ELECTRONIC VISION AID DEVICE AND AUTOMATIC IMAGE MAGNIFICATION METHOD THEREOF

TECHNICAL FIELD

The present invention relates to the field of intelligent medical equipment, in particular to a head-mounted electronic vision aid device and A method for automatic image magnification thereof.

BACKGROUND ART

Macular degeneration is a common medical disease, which is especially common in the elderly. People with macular degeneration usually have damaged or dysfunctional retina (especially the macula of the retina). The macula usually has the highest resolution of eyes. Usually, the damaged or dysfunctional macula may not respond normally to the light in front of a person. As a result, the patient may have blurred vision or no vision at the center of the visual field or a certain area around it. The macular degeneration may limit the ability of face identification, driving, reading and other aspects of the person. The deterioration of the macula may extend outward from the center of the retina, however, it is unlikely to affect the peripheral area of the retina.

With the technological development of AR/VR wearable devices, more and more head-mounted devices (HMD) are designed to capture images in surrounding scenes of users, display the captured scenes in real time through AR display systems, and can amplify or modify the displayed scenes. The head-mounted devices (HMD) usually comprise image zooming units that allow the users to amplify the contents captured by cameras to compensate for the deficiency of resolution. In the prior art, the adjustment of the MID magnification is usually implemented manually by the users through buttons on remote controllers or on the devices themselves or by touch and sliding. When the user is interested in several target objects in the visual field but at different distances, it is not difficult to imagine that the user needs to manually adjust the magnification among these target objects all the time to see the target objects clearly. For low vision users, the manual adjustment steps are cumbersome. In addition, when it is necessary to switch between two preset magnifications (for example, when the wearer is reading and occasionally talking to a person sitting across the table), the manual adjustment of the magnification is usually inaccurate and slow. In particular, the visually impaired users often cannot intuitively determine the magnification required for an object within a certain distance. Therefore, there is an urgent need for an improved head-mounted electronic assisted visual device to solve the deficiencies in the prior art.

SUMMARY OF THE INVENTION

In order to solve the technical problems of cumbersome, inaccurate and slow speed of manually adjusting the magnification by a user in the prior art, the present invention aims to provide a head-mounted electronic vision aid device that can automatically amplify the image of a target object accurately, intuitively and quickly according to the demand of the user.

In order to achieve one of the above-mentioned purposes of the present invention, one embodiment of the present invention provides a head-mounted electronic vision aid device, including a memory unit, a processing unit, and an image zooming unit, and further including at least one ranging unit configured to obtain distance data between a target object of interest to the user and the device and/or three-dimensional profile data of the object and output the data to the processing unit;

the memory unit configured to store a correspondence table between the distance data and the magnification of the image zooming unit;

the processing unit configured to confirm the target object of interest to the user, perform operations on the distance data and/or the three-dimensional profile data of the object, and output an magnification matching the distance data to the image zooming unit according to the correspondence table; and the image zooming unit configured to automatically adjust to the matching magnification.

As a further improvement of one embodiment of the present invention, the head-mounted electronic vision aid device further comprising a display unit, and the target object of interest to the user is set within the range of a checkbox visible to the user of the display unit.

As a further improvement of one embodiment of the present invention, the checkbox can be configured to be automatically selected by the processing unit or selected by the user on demand.

As a further improvement of one embodiment of the present invention, when the matching magnification is greater than a set value, the checkbox automatically disappears or fades on the display unit.

As a further improvement of one embodiment of the present invention, the distance data of the correspondence table comprising one or more distance intervals, and the one or more distance intervals respectively correspond to preset magnifications.

As a further improvement of one embodiment of the present invention, the head-mounted electronic vision aid device further comprising a user adjustment unit including an adjustment section for user interaction with the device, with the adjustment section being able to output an magnification adjustment signal to the processing unit, the processing unit modifies the magnification in the correspondence table according to the adjustment signal, and the memory unit stores and automatically updates to the modified correspondence table.

As a further improvement of one embodiment of the present invention, the adjustment section is a touch operation panel provided on the device, or a voice module, a gesture recognition module, an EEG sensing module and a myoelectric sensing module capable of inputting a control commands to automatically adjust the magnification of the image zooming unit.

As a further improvement of one embodiment of the present invention, the ranging unit comprising one or the combination of more of a micro electro mechanical system MEMS sensor, an ultrasonic sensor, a laser ranging sensor, a millimeter wave sensor, a radar ranging sensor, a structured light sensor, an optical ranging sensor and a camera.

As a further improvement of one embodiment of the present invention, the image zooming unit comprising a camera, a microdisplay and/or a microprojector.

As a further improvement of one embodiment of the present invention, the number of the ranging units is greater than or equal to 2, and the processing unit performs one or more operations of classification, weight assignment or averaging on the distance data measured by the plurality of ranging units for obtaining the optimal distance data between the target object and the device.

The present invention further provides A method for automatic image magnification of a head-mounted electronic vision aid device, the device including a memory unit, a processing unit, an image zooming unit and a ranging unit, and the method including the following steps:

determining a target object of interest to a user;

storing, by the memory unit, a correspondence table between the distance data and the magnification of the image zooming unit;

obtaining, by the ranging unit, distance data between the target object of interest to the user and the device and/or three-dimensional profile data of the object, and outputting the data to the processing unit;

performing, by the processing unit, operations on the distance data, and outputting an magnification matching the distance data to the image zooming unit according to the correspondence table; and automatically adjusting, by the image zooming unit, to the matching magnification.

As a further improvement of one embodiment of the present invention, in the step of determining the target object of interest to the user, the target object of interest to the user is set within the range of a checkbox visible to the user.

As a further improvement of one embodiment of the present invention, the checkbox is automatically selected by the processing unit or is selected by the user on demand.

As a further improvement of one embodiment of the present invention, the distance data of the correspondence table comprising one or more distance intervals respectively corresponding to preset magnifications, the processing unit determines the distance data obtained by the ranging unit falling into which interval of the plurality of distance intervals, and outputs the magnification corresponding to the interval to the image zooming unit.

As a further improvement of one embodiment of the present invention, the device further comprising a user adjustment unit including an adjustment section for user interaction with the device, the adjustment section being able to output an magnification adjustment signal to the processing unit, the processing unit modifies the magnification in the correspondence table according to the adjustment signal, and the memory unit stores and automatically updates to the modified correspondence table.

As a further improvement of one embodiment of the present invention, the ranging unit comprising one or the combination of more of a micro electro mechanical system MEMS sensor, an ultrasonic sensor, a laser ranging sensor, a millimeter wave sensor, a radar ranging sensor, a structured light sensor, an optical ranging sensor and a camera.

As a further improvement of one embodiment of the present invention, the image zooming unit comprising a camera, a microdisplay and/or a microprojector.

As a further improvement of one embodiment of the present invention, the number of the ranging units is greater than or equal to 2, and the processing unit performs one or more operations of classification, weight assignment or averaging on the distance data measured by the plurality of ranging units for obtaining the optimal distance data between the target object and the device.

As a further improvement of one embodiment of the present invention, after the processing unit receives the magnification adjustment signal output by the user adjustment unit, the processing unit instantly modifies the magnification in the correspondence table according to the adjustment signal, and the memory unit stores and automatically updates to the modified correspondence table.

As a further improvement of one embodiment of the present invention, when the adjustment signal output by the user adjustment unit is held for more than a preset time, the processing unit modifies the magnification in the correspondence table according to the adjustment signal, and the memory unit stores and automatically updates to the modified correspondence table.

As a further improvement of one embodiment of the present invention, the adjustment section is a touch operation panel provided on the device, or a voice module, a gesture recognition module, an EEG sensing module and a myoelectric sensing module capable of inputting a control commands to automatically adjust the magnification of the image zooming unit.

In which:

100, head-mounted electronic vision aid device; 101, wearable bracket; 102, memory unit; 103, processing unit; 104, image zooming unit; 105, ranging unit; 106, adjustment section; 107, display unit; 108, checkbox.

DETAILED DESCRIPTION OF THE EMBODIMENTS

The embodiments of the present invention are described in detail below. Examples of the embodiments are shown in the drawings, wherein the same or similar reference signs indicate the same or similar elements or elements with the same or similar functions. The embodiments described below with reference to the drawings are exemplary, and are intended to explain the present invention, but cannot be construed as limitations to the present invention.

The technical solutions of the present invention will be further described below in conjunction with the drawings and specific embodiments.

Figure 1:
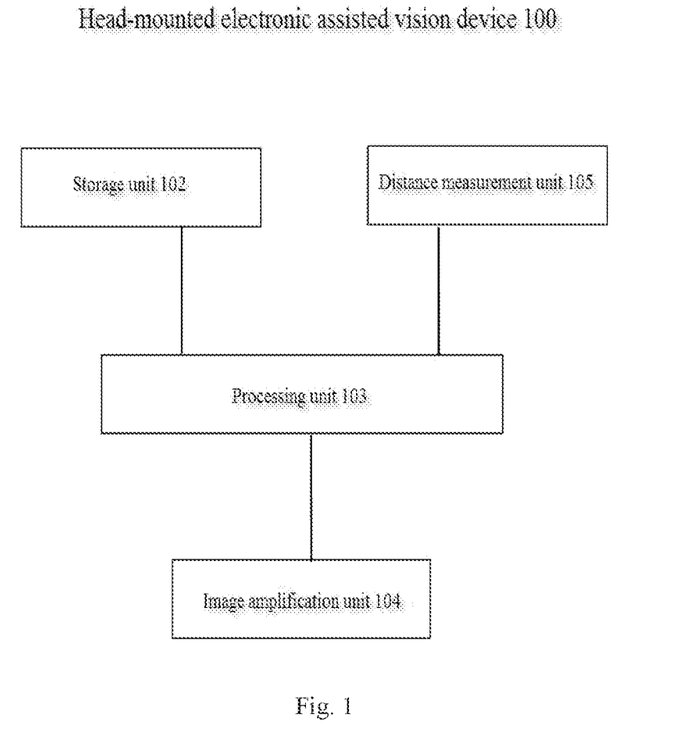
FIG. 1 is a schematic diagram of a hardware module of one embodiment of a head-mounted electronic vision aid device 100.

Referring to FIG. 1, one embodiment of the present invention provides a head-mounted electronic vision aid device 100, including a memory unit 102, a ranging unit 105 and an image zooming unit 104, which are connected with a processing unit 103. The ranging unit 105 is configured to obtain distance data between a target object of interest to a user and the device 100 and/or three-dimensional profile data of the object and output the data to the processing unit 103. The memory unit 102 can be configured to store a correspondence table between the distance data and the magnification of the image zooming unit 104; and the processing unit 103 confirms the target object of interest to the user, performs operations on the distance data and/or the three-dimensional profile data of the object obtained by the ranging unit 105, and outputs an magnification matching the distance data to the image zooming unit 104 according to the correspondence table. After receiving the signal from the processing unit 103, the image zooming unit 104 can automatically adjust magnification thereof to the matching magnification. Especially for visually impaired users, accurate, intuitive and rapid automatic magnification of the target objects of interest is realized on demand. Compared with the prior art, the repeated and tedious manual adjustment is avoided.

Figure 4:
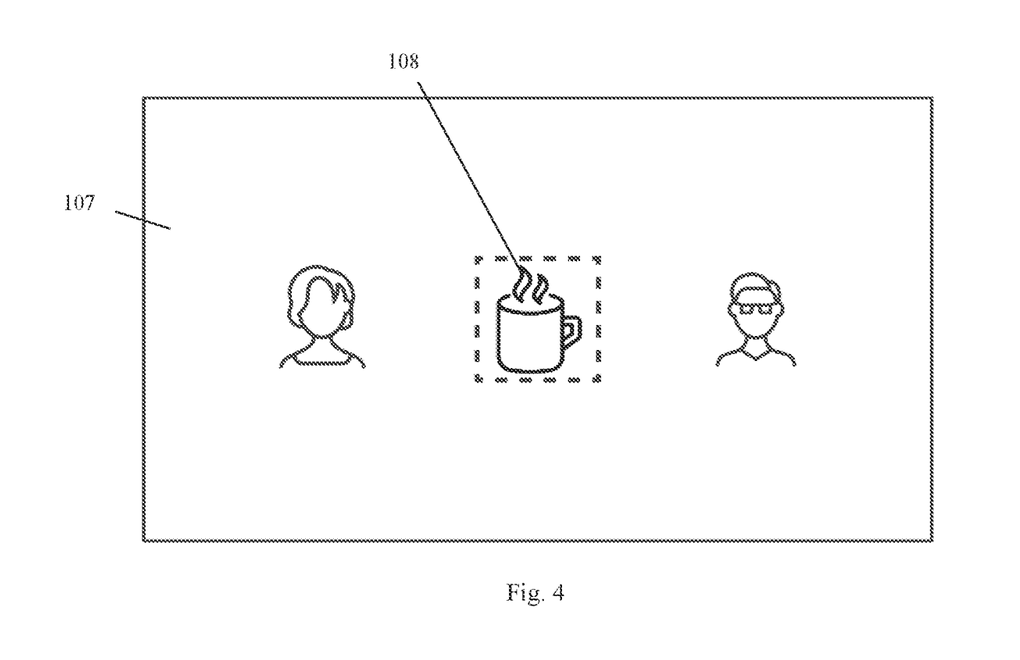
FIG. 4 is a schematic structural diagram of a checkbox of determining a target object of interest to a user in the head-mounted electronic vision aid device 100.

The target object of interest to the user is set within the range of a checkbox 108 visible to the user of the display unit 107, so that the user can confirm the target object of interest to the user that needs to be amplified in a very intuitive manner. The checkbox 108 in this embodiment has high contrast, for example, the target object of interest to the user is arranged in a red check box of the display unit, so that the target object of interest to the user has advantages in terms of color contrast, clarity and the like. Of course, the checkbox 108 can also be set to other different colors with high contrast according to different screen display parameters.

The memory unit 102 is intended to allow the long-term memory of computer program instructions and other data. The memory unit 102 can comprise various types of non-volatile information memory devices, such as a flash memory module, a hard disk drive, or a solid state drive. The head-mounted electronic vision aid device 100 further comprising a power supply located in the main body to supply power to various components of the head-mounted electronic vision aid device 100. In some specific embodiments, the power supply can comprise any suitable type of batteries, such as a rechargeable battery. In the specific embodiments including the battery, the head-mounted electronic vision aid device 100 can comprise components that facilitate wired or wireless recharging.

The ranging unit 105 can be one or the combination of more of a micro electro mechanical system MEMS sensor, an ultrasonic sensor, a laser ranging sensor, a millimeter wave sensor, a radar ranging sensor, a structured light sensor, an optical ranging sensor and a camera. The ranging unit can be installed on a plane of the head-mounted electronic vision aid device 100 substantially parallel to the eyes of the user. In a preferred embodiment, the number of the ranging units is greater than or equal to 2, and the processing unit 103 performs one or more operations of classification, weight assignment or averaging on the distance data measured by the plurality of ranging units 105 for obtaining the optimal distance data between the target object and the device 100. The image zooming unit 104 can be a camera, a microdisplay and/or a microprojector, wherein the microprojector can be a waveguide type miniature projection system or a reflection type miniature projection system. The image zooming unit 104 in this embodiment is a camera.

In this embodiment, the distance data of the correspondence table comprising a set of one or more distance intervals, and the one or more distance intervals respectively correspond to preset magnifications. If the processing unit 103 calculates that the distance between the target object and the device is 0.5 m, according to the correspondence table, it is concluded that the automatic magnification of the camera should be automatically adjusted to 1.5.

Figure 3:
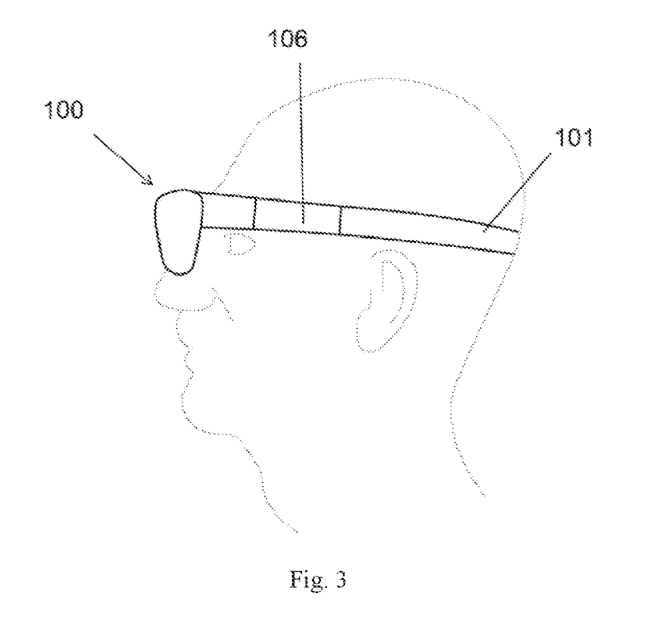
FIG. 3 is a schematic structural diagram of one embodiment of the head-mounted electronic vision aid device 100.

Referring to FIG. 3, in one embodiment of the present invention, the head-mounted electronic vision aid device 100 further comprising a wearable bracket 101, the memory unit 102, the ranging unit 105 and the image zooming unit 104 can be arranged on the wearable bracket 101, the processing unit 103 can be arranged on the wearable bracket 101, and can also be arranged on a device other than the wearable bracket 101, such as a remote controller or an external mobile terminal device, such as a smart phone. The head-mounted electronic vision aid device 100 further comprising a user adjustment unit, the user adjustment unit 105 comprising an adjustment section 106 for user interaction with the device 100, the adjustment section 106 can output an magnification adjustment signal to the processing unit 103, the processing unit 103 modifies the magnification in the correspondence table according to the adjustment signal, and the memory unit 102 stores and automatically updates to the modified correspondence table.

In a preferred embodiment, the adjustment section 106 of the user adjustment unit is a touch operation panel that is integrally arranged on the wearable bracket 101, and the adjustment of the image magnification is realized by the user by operating the touch operation panel. After the ranging unit 105 inputs the measured distance between the target object and the device (for example, 0.5 m) into the processing unit 103, the processing unit 103 obtains that the magnification is 1.5 according to the corresponding relationship between the distance and the magnification in the correspondence table. At this time, if the user feels that it is necessary to further modify the magnification, he can use the touch operation panel to further manually adjust the magnification, for example, modify the magnification to 1.4, at this time, the memory unit 102 should replace the previously preset magnification 1.5 with the modified magnification 1.4. In this way, the correspondence table is continuously and automatically optimized according to the needs of the user, so that the correspondence table better conforms to the actual needs of different users.

In another preferred embodiment, the adjustment section 106 can also be a voice module, and the voice module can input a voice instruction into the processing unit to automatically adjust the magnification of the image zooming unit. For example, the voice module inputs a voice instruction of the magnification, amplifying or shrinking needed by the user into the processing unit, and the magnification of the image zooming unit can be automatically adjusted without the manual adjustment of the user. In other preferred embodiments, the adjustment section 106 can also be a gesture recognition module, an EEG sensing module and a myoelectric sensing module capable of inputting a control commands to automatically adjust the magnification of the image zooming unit.

The checkbox 108 can be configured to be automatically selected by the processing unit 103 or selected by the user on demand. When being automatically selected by the processing unit 103, the checkbox 108 can always be arranged in a central area of the display unit 107 by default by the system. When the user needs to amplify the target object of interest, the user can rotate the head to move the HMD, so that the target object of interest is always in the red check box of the display unit. When the checkbox is selected by the user on demand, the user can select the target object of interest through the adjustment section 106, for example, the touch operation panel, and the target object of interest to the user can also be selected through voice module input.

For example, if there are multiple objects such as a human face and a water cup at different distances in the visual field of the user, the user can use the checkbox 108 to select the target object of interest in different ways. In one embodiment, the user can operate the checkbox 108 to select the water cup through the touch operation panel; in another embodiment, the user can control the checkbox 108 to select the water cup through voice input; and in another embodiment, the user can control the checkbox 108 to select the water cup by using user past use data stored in the cloud. After the checkbox 108 determines the target object of interest to the user, the ranging unit 105 measures the distance data, and automatically obtains the magnification according to the correspondence table of the distance data and the magnification, and the zooming unit automatically amplifies the water cup to the magnification to assist the user to automatically adjust the magnification of the image zooming unit without the need for manual adjustment by the user and without losing the target object of interest. Preferably, in order to prevent the amplified image of the object from being amplified inappropriately, when the automatically matching magnification is greater than a set value, the checkbox automatically disappears or fades on the display unit, and the becoming shallow here comprising that the color fades or the low contrast makes it difficult to distinguish the checkbox in the visual field of the user.

Figure 2:
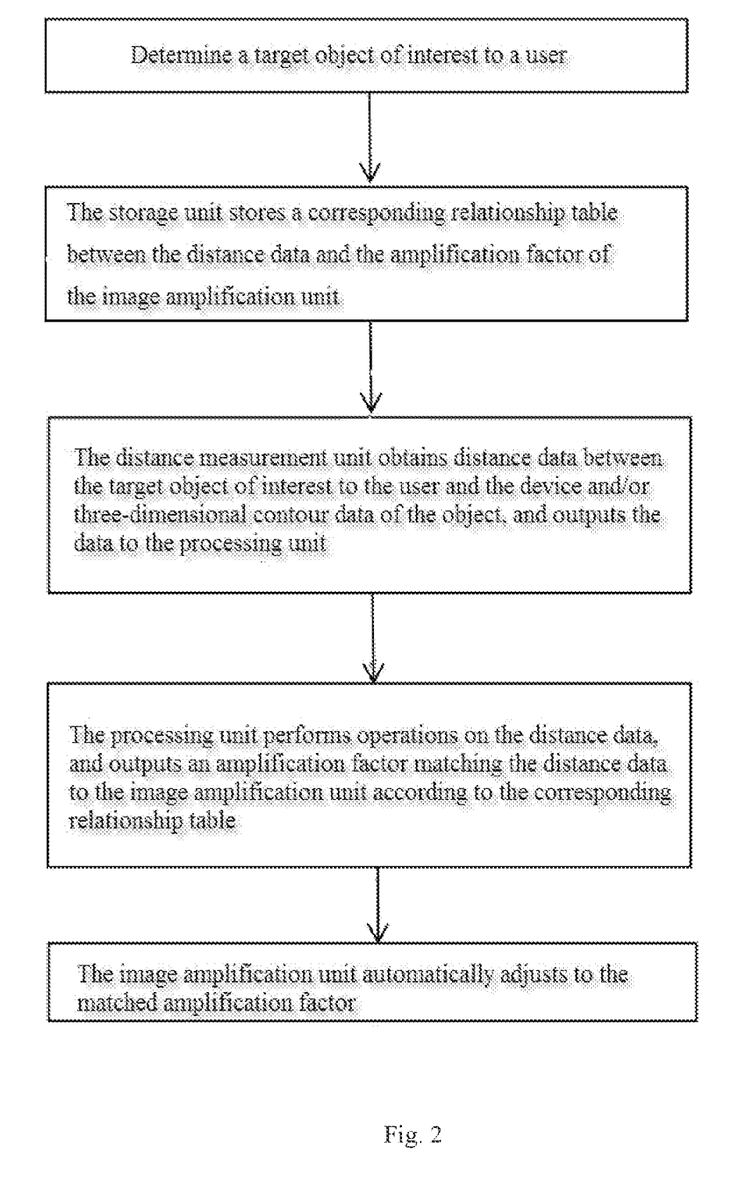
FIG. 2 is a schematic diagram of software flow of one embodiment of the head-mounted electronic vision aid device 100.

Referring to FIG. 2, the embodiment of the present invention provides A method for automatic image magnification of a head-mounted electronic vision aid device 100. The device 100 comprising a wearable bracket 101, and a memory unit 102, a processing unit 103, an image zooming unit 104 and a ranging unit 105, which are arranged on the wearable bracket 101, and the method comprising the following steps:

determining a target object of interest to a user; specifically, selecting and confirming the target object of interest to the user by arranging the target object of interest to the user within the range of a checkbox visible to the user.

The memory unit 102 stores a correspondence table between the distance data and the magnification of the image zooming unit 104;

the ranging unit 105 obtains distance data between the target object of interest to the user and the device 100 and/or three-dimensional profile data of the object, and outputs the data to the processing unit 103;

the processing unit 103 performs operations on the distance data, and outputs an magnification matching the distance data to the image zooming unit 104 according to the correspondence table; and the image zooming unit 104 can automatically adjust the magnification thereof to the matching magnification after receiving the signal of the processing unit 103. For visually impaired users, accurate, intuitive and rapid automatic magnification of the target objects of interest is realized on demand. Compared with the prior art, the repeated and tedious manual adjustment is avoided.

The ranging unit 105 can be one or the combination of more of a micro electro mechanical system MEMS sensor, an ultrasonic sensor, a laser ranging sensor, a millimeter wave sensor, a radar ranging sensor, a structured light sensor, an optical ranging sensor and a camera. The ranging unit is installed on a plane of the head-mounted electronic vision aid device 100 substantially parallel to the eyes of the user. In a preferred embodiment, the number of the ranging units is greater than or equal to 2, and the processing unit 103 performs one or more operations of classification, weight assignment or averaging on the distance data measured by the plurality of ranging units 105 for obtaining the optimal distance data between the target object and the device 100.

The image zooming unit 104 can be a camera, a microdisplay and/or a microprojector, wherein the microprojector can be a waveguide type miniature projection system or a reflection type miniature projection system. The image zooming unit 104 in this embodiment is a camera. The number of the ranging units is greater than or equal to 2, and the processing unit performs one or more operations of classification, weight assignment or averaging on the distance data measured by the plurality of ranging units for obtaining the optimal and most accurate distance data between the target object and the device.

In this embodiment, the distance data of the correspondence table comprising one or more distance intervals, and the one or more distance intervals correspond to preset magnifications. The processing unit determines the distance data obtained by the ranging unit falling into which interval of the plurality of distance intervals, and outputs the magnification corresponding to the interval to the image zooming unit. If the processing unit 103 calculates that the distance between the target object and the device is 0.5 m, according to the correspondence table, it is concluded that the automatic magnification of the camera should be automatically adjusted to 1.5.

The device 100 further comprising a user adjustment unit, the user adjustment unit comprising an adjustment section 106 for user interaction with the device 100, the adjustment section 106 can output an magnification adjustment signal to the processing unit 103, the processing unit 103 modifies the magnification in the correspondence table according to the adjustment signal, and the memory unit 102 stores and automatically updates to the modified correspondence table.

In a preferred embodiment, the adjustment section 106 of the user adjustment unit is a touch operation panel that is integrally arranged on the wearable bracket 101, and the adjustment of the image magnification is realized by the user by operating the touch operation panel. After the ranging unit 105 inputs the measured distance between the target object and the device (for example, 0.5 m) into the processing unit 103, the processing unit 103 obtains that the magnification is 1.5 according to the corresponding relationship between the distance and the magnification in the correspondence table. At this time, if the user feels that it is necessary to further modify the magnification, he can use the touch operation panel to manually adjust a new magnification, the processing unit 103 can instantly modify the magnification as the magnification in the new correspondence table according to the adjustment signal, for example, modify the magnification to 1.4, at this time, the memory unit 102 should replace the previously preset magnification 1.5 with the modified magnification 1.4. In other embodiments, the processing unit 103 can also judge whether the holding time of the adjustment signal exceeds a preset time (for example, 2 seconds, 3 seconds, or 5 seconds), if the holding time exceeds the preset time, the processing unit adjusts the magnification factor from the original 1.5 in the original correspondence table to 1.4 in the new correspondence table, so that continuous machine learning and automatic optimization of the correspondence table are realized according to the demands of the user, and then the correspondence table better conforms to the actual needs of different users. In another preferred embodiment, the correspondence table can also be collected and stored in the cloud at any time. By analyzing the user data stored and updated in the cloud, a more suitable magnification factor can be obtained according to different user habits, thereby greatly improving the user experience.

In another preferred embodiment, the adjustment section 106 can also be a voice module, and the voice module can input a voice instruction into the processing unit to automatically adjust the magnification of the image zooming unit. For example, the voice module inputs a voice instruction of the magnification, amplifying or shrinking needed by the user into the processing unit. When the processing unit 103 receives the voice instruction, the processing unit 103 modifies the magnification factor in the correspondence table according to the magnification factor modified by the user, and the memory unit 102 stores and automatically updates to the modified correspondence table. In this way, the user can independently adjust the magnification factor to a suitable magnification factor according to his own needs and vision conditions, the magnification factor of the image magnification unit can be automatically adjusted without the manual adjustment of the user, the device 100 intelligently records and updates a better correspondence table suitable for the user, so that the use is more user-friendly and meets the needs of different low-vision users. In other preferred embodiments, the adjustment section 106 can also be a gesture recognition module, an EEG sensing module or a myoelectric sensing module capable of inputting a control commands to automatically adjust the magnification of the image zooming unit.

The checkbox 108 can be automatically selected by the processing unit 103 or selected by the user on demand. When being automatically selected by the processing unit 103, the checkbox 108 can always be arranged in a central area of the display unit 107 by default by the system. When the user needs to amplify the target object of interest, the user can rotate the head to move the HMD, so that the target object of interest is always in the red check box of the display unit. When the checkbox is selected by the user on demand, the user can select the target object of interest through the adjustment section 106, for example, the touch operation panel, and the target object of interest to the user can also be selected through voice module input.

For example, if there are multiple objects such as a human face and a water cup at different distances in the visual field of the user, the user can use the checkbox 108 to select the target object of interest in different ways. In one embodiment, the user can operate the checkbox 108 to select the water cup through the touch operation panel; in another embodiment, the user can control the checkbox 108 to select the water cup through voice input; and in another embodiment, the user can control the checkbox 108 to select the water cup by using user past use data stored in the cloud. After the checkbox 108 determines the target object of interest to the user, the ranging unit 105 measures the distance data, and automatically obtains the magnification according to the correspondence table of the distance data and the magnification, and the zooming unit automatically amplifies the water cup to the magnification to assist the user to automatically adjust the magnification of the image zooming unit without the need for manual adjustment by the user and without losing the target object of interest. Preferably, in order to prevent the amplified image of the object from being amplified inappropriately, when the automatically matching magnification is greater than a set value, the checkbox automatically disappears or fades on the display unit, and the becoming shallow here comprising that the color fades or the low contrast makes it difficult to distinguish the checkbox in the visual field of the user.

It should be understood that although this specification is described in accordance with the embodiments, not each embodiment only comprising an independent technical solution. This narration in the specification is only for the sake of clarity, those skilled in the art should regard the specification as a whole, and the technical solutions in various embodiments can also be appropriately combined to form other embodiments that can be understood by those skilled in the art.

A series of detailed descriptions listed above are only specific descriptions of the feasible embodiments of the present invention, they are not intended to limit the protection scope of the present invention, and any equivalent embodiments or modifications, made without departing from the spirit of the present invention, shall all fall within the protection scope of the present invention.

The invention claimed is:

1. A head-mounted electronic vision aid device, comprising:
 a memory unit;
 a processing unit;
 an image zooming unit;
 a user adjustment unit comprising an adjustment section for user interaction with the device; and
 at least one ranging unit configured to obtain distance data between a target object of interest to a user and the device and to output the distance data to the processing unit, wherein
  the memory unit is configured to store a table of correspondence relationships between distance and magnification for the image zooming unit,
  the processing unit is configured to identify the target object of interest to the user, and to perform one or more operations on the distance data, and to output a magnification matching the distance data to the image zooming unit according to the correspondence table,
  the image zooming unit is configured to automatically adjust to the matching magnification, and
  the adjustment section is able to output a magnification adjustment signal to the processing unit, the processing unit modifying the magnification in the correspondence table according to the adjustment signal, and the memory unit stores and automatically updates to the modified correspondence table.

2. The head-mounted electronic vision aid device according to claim 1, further comprising:
 a display unit, wherein the target object of interest to the user is set within a user-visible checkbox of the display unit.

3. The head-mounted electronic vision aid device according to claim 2, wherein the checkbox can be configured to be automatically selected by the processing unit or selected by the user on demand.

4. The head-mounted electronic vision aid device according to claim 2, wherein when the matching magnification is greater than a set value, the checkbox automatically disappears or fades on the display unit.

5. The head-mounted electronic vision aid device according to claim 1, wherein the correspondence table comprises a plurality of distance intervals that each correspond to a respective preset magnification.

6. The head-mounted electronic vision aid device according to claim 1, wherein the adjustment section is one or more of a touch operation panel provided on the device, a voice module, a gesture recognition module, an EEG sensing module, and a myoelectric sensing module capable of inputting control commands to automatically adjust the magnification of the image zooming unit.

7. The head-mounted electronic vision aid device according to claim 1, wherein the at least one ranging unit comprises one or more of a micro electro mechanical system (MEMS) sensor, an ultrasonic sensor, a laser ranging sensor, a millimeter wave sensor, a radar ranging sensor, a structured light sensor, and an optical ranging sensor.

8. The head-mounted electronic vision aid device according to claim 1, wherein the image zooming unit comprises one or more of a camera, a microdisplay, and a microprojector.

9. A head-mounted electronic vision aid device, comprising:
- a memory unit;
- a processing unit;
- an image zooming unit; and
- at least one ranging unit configured to obtain distance data between a target object of interest to a user and the device and to output the distance data to the processing unit, wherein
  - the memory unit is configured to store a table of correspondence relationships between distance and magnification for the image zooming unit,
  - the processing unit is configured to identify the target object of interest to the user, and to perform one or more operations on the distance data, and to output a magnification matching the distance data to the image zooming unit according to the correspondence table, and
  - the image zooming unit is configured to automatically adjust to the matching magnification,
  - the at least one ranging unit is a plurality of ranging units, and
  - the one or more operations performed on the distance data by the processing unit includes performing one or more operations of classification, weight assignment, and averaging on the distance data obtained by the plurality of ranging units to obtain optimal distance data between the target object and the device, and the matching magnification being the magnification that matches the optimal distance data according to the correspondence table.

10. A method for automatic image magnification of a head-mounted electronic vision aid device, the device comprising a memory unit, a processing unit, an image zooming unit, a user adjustment unit, and at least one ranging unit, a table of correspondence relationships between distance and magnification for the image zooming unit stored in the memory unit, and the method comprising:
- determining a target object of interest to a user;
- obtaining, by the at least one ranging unit, distance data between the target object of interest to the user and the device, and outputting the distance data to the processing unit;
- performing, by the processing unit, one or more operations on the distance data, and outputting a magnification matching the distance data to the image zooming unit according to the correspondence table; and
- automatically adjusting, by the image zooming unit, to the matching magnification,
  - wherein the user adjustment unit comprises an adjustment section for user interaction with the device, the adjustment section being able to output a magnification adjustment signal to the processing unit, the processing unit modifies the magnification in the correspondence table according to the adjustment signal, and the memory unit stores and automatically updates to the modified correspondence table.

11. The method for automatic image magnification of the head-mounted electronic vision aid device according to claim 10, in the determining of the target object of interest to the user, the target object of interest to the user is set within the range of a checkbox visible to the user.

12. The method for automatic image magnification of the head-mounted electronic vision aid device according to claim 11, wherein the checkbox is automatically selected by the processing unit or by the user on demand.

13. The method for automatic image magnification of the head-mounted electronic vision aid device according to claim 10, wherein correspondence table comprises a plurality of distance intervals that each corresponding to a respective preset magnification, and the processing unit determines the distance data obtained by the at least one ranging unit falling into which interval of the plurality of distance intervals, and outputs the respective preset magnification corresponding to the interval to the image zooming unit.

14. The method for automatic image magnification of the head-mounted electronic vision aid device according to claim 10, wherein the at least one ranging unit comprises one or more of a micro electro mechanical system (MEMS) sensor, an ultrasonic sensor, a laser ranging sensor, a millimeter wave sensor, a radar ranging sensor, a structured light sensor, and an optical ranging sensor.

15. The method for automatic image magnification of the head-mounted electronic vision aid device according to claim 10, wherein the image zooming unit comprises one or more of a camera, a microdisplay, and a microprojector.

16. The method for automatic image magnification of the head-mounted electronic vision aid device according to claim 10, wherein
- the at least one ranging unit is a plurality of ranging units,
- the performing, by the processing unit, of the one or more operations on the distance data includes one or more operations of classification, weight assignment, and averaging on the distance data obtained by the plurality of ranging units to obtain optimal distance data between the target object and the device, and the matching magnification being the magnification that matches the optimal distance data according to the correspondence table.

17. The method for automatic image magnification of the head-mounted electronic vision aid device according to claim 10, wherein when the processing unit receives the magnification adjustment signal output by the user adjustment unit, the processing unit instantly modifies the magnification in the correspondence table according to the adjustment signal, and the memory unit stores and automatically updates to the modified correspondence table.

18. The method for automatic image magnification of the head-mounted electronic vision aid device according to claim 10, wherein when the adjustment signal output by the user adjustment unit is held for more than a preset time, the processing unit modifies the magnification in the correspondence table according to the adjustment signal, and the memory unit stores and automatically updates to the modified correspondence table.

19. The method for automatic image magnification of the head-mounted electronic vision aid device according to claim 10, wherein the adjustment section is one or more of a touch operation panel provided on the device, a voice module, a gesture recognition module, an EEG sensing module, and a myoelectric sensing module capable of inputting a control commands to automatically adjust the magnification of the image zooming unit.

* * * * *